United States Patent [19]

Parsons

[11] Patent Number: 5,115,061
[45] Date of Patent: May 19, 1992

[54] N-PROPIONITRILE MALEIMIDES, PREPARATION PROCESS AND POLYMERS THEREOF

[75] Inventor: Charles F. Parsons, Little Hocking, Ohio

[73] Assignee: General Electric Company, N.Y.

[21] Appl. No.: 580,447

[22] Filed: Sep. 10, 1990

Related U.S. Application Data

[62] Division of Ser. No. 401,296, Aug. 31, 1989, abandoned.

[51] Int. Cl.$^5$ .............................................. C08F 22/40
[52] U.S. Cl. ................................................... 526/262
[58] Field of Search ........................................ 526/262

[56] References Cited

U.S. PATENT DOCUMENTS 2,444,536  5/1946  Searle ................................. 260/313

OTHER PUBLICATIONS

*Organic Reactions*, vol. V, Chapter 2 (John Wiley & Sons, New York, 1949), pp. 79-89 and 113.
*The Chemistry of Acrylonitrile*, (American Cyanamide Company, 1959), pp. 17-27.
*Maleic Anhydride*, Chapter 3 (Plenum Press, New York, 1982), pp. 81-91.
Kucharski et al, "Synthesis of N-(2-cyanoethyl)-1,-2-dicarboximides", *Chemia Stosowana*, XXXii, 1, pp. 161-170 (1988), and corresponding to Chemical Abstract 112 11; 98317n.

*Primary Examiner*—Joseph L. Schofer
*Assistant Examiner*—Alex H. Walker
*Attorney, Agent, or Firm*—Lowe, Price, LeBlanc & Becker

[57]  ABSTRACT

Novel compounds comprising N-propionitrile maleimides are formed by the reaction of an N-propionitrile maleamic acid and acetic anhydride. N-propionitrile maleamic acids are formed by the reaction of an aminopropionitrile with maleic anhydride. The novel maleimides may be homopolymerized or copolymerized with one or more comonomers.

3 Claims, No Drawings

N-PROPIONITRILE MALEIMIDES, PREPARATION PROCESS AND POLYMERS THEREOF

This application is a divisional of application Ser. No. 401,296, filed Aug. 31, 1989, now abandoned.

FIELD OF THE INVENTION

The present invention relates to novel compounds comprising N-propionitrile maleimides. The present invention also relates to methods for preparing the N-propionitrile maleimides and to polymers formed from at least one monomer comprising an N-propionitrile maleimide.

BACKGROUND OF THE INVENTION

Cyanoethylation is a well known chemical reaction involving the addition of acrylonitrile to an inorganic or organic compound containing a labile hydrogen atom. Cyanoethylation reactions are disclosed, for example in *Organic Reactions*, Vol. V, Chapter 2 (John Wiley & Sons, New York, 1949) and *The Chemistry of Acrylonitrile* (American Cyanamide Company, 1959), both of which disclosures are incorporated herein by reference. However, attempts to prepare the cyanoethylation product of maleimide by the reaction of maleimide and acrylonitrile have been unsuccessful.

On the other hand, the Searle U.S. Pat. No. 2,444,536 discloses a process for the synthesis of N-arylmaleimides wherein an aryl maleamic acid is treated with acetic anhydride in the presence of fused sodium acetate at a temperature of 80° to 100° C. However, Searle provides no teaching relating to the preparation of N-propionitrile maleimides.

SUMMARY OF THE INVENTION

Accordingly, it is an object of the invention to provide novel compounds comprising N-propionitrile maleimides and to provide a process for preparing N-propionitrile maleimides. It is a further object of the invention to provide novel N-propionitrile maleamic acids from which the N-propionitrile maleimides may be formed and methods for preparing the N-propionitrile maleamic acids. An additional object of the invention is to provide N-propionitrile maleimide polymers and copolymers which may be useful in forming plastic products and which may provide heat resistance and compatibility to plastic compositions.

These and additional objects are provided by the N-propionitrile maleimide compounds of the present invention. The N-propionitrile maleimides are produced by reacting an N-propionitrile maleamic acid with acetic anhydride. The N-propionitrile maleamic acids are prepared by reacting an aminopropionitrile with maleic anhydride. The N-propionitrile maleimide compounds of the invention may be useful in preparing thermoplastic polymers and copolymers. The maleimides and the maleamic acids from which they are produced may also be useful in various pharmaceutical and insecticidal applications.

These and additional objects and advantages provided by the compounds, methods and compositions of the present invention will be more fully understood in view of the following detailed description.

DETAILED DESCRIPTION

The novel compounds of the present invention comprise N-propionitrile maleimides. Preferably, the compounds comprise N-(beta-propionitrile) maleimide of the general formula (I):

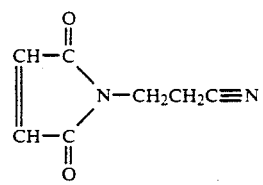

The maleimide compounds of the invention are prepared from the corresponding N-propionitrile maleamic acids by reaction of the corresponding acids with acetic anhydride. More specifically, compound (I) as set forth above is prepared from N-(beta-propionitrile) maleamic acid of general formula (II):

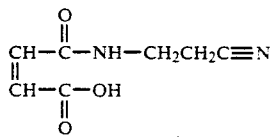

In preparing the maleimide compounds of the invention, the appropriate maleamic acid is reacted with acetic anhydride. The acetic anhydride is preferably employed in a stoichiometric excess amount, and the reaction is preferably conducted in the presence of sodium acetate. The reaction of the maleamic acid and the acid anhydride is preferably conducted under mild heating in order to cyclize or dehydrate the maleamic acid. For example, the reaction may be conducted at a temperature in the range of from about 80° C. to about 100° C.

The N-propionitrile maleamic acids are also novel compounds and may be prepared by reacting the appropriate aminopropionitrile with maleic anhydride. In a preferred embodiment, the aminopropionitrile comprises beta-aminopropionitrile, whereby the maleamic acid which is produced comprises N-(beta-propionitrile) maleamic acid and the resulting maleimide comprises N-(beta-propionitrile) maleimide. The reaction of the aminopropionitrile with maleic anhydride to produce the maleamic acid may be conducted at room temperature or at a reduced temperature. Throughout the present specification and claims, the reference to an elevated temperature or a reduced temperature is with reference to room temperature of approximately 25° C. The reaction of the aminopropionitrile and maleic anhydride is preferably conducted in an organic solvent such as an ether or chloroform.

Generally, beta-aminopropionitrile is not commercially available but may be produced as the cyanoethylation product of ammonia and acrylonitrile. The cyanoethylation reaction may be conducted in an aqueous or gaseous phase and the liquid beta-aminopropionitrile product may be isolated by vacuum distillation.

The N-propionitrile maleimide compounds of the invention may be homopolymerized and/or copolymerized with one or more comonomers. The polymers are suitable for use in various thermoplastic polymer applications for providing compositions exhibiting heat resistance and compatibility. Comonomers which may be used in combination with the maleimide compounds of the invention include, among others, styrene, substituted styrenes, acrylonitrile, alkyl acrylates, alkyl methacrylates, maleic anhydride, maleimide and N-phenyl maleimide. The polymerization techniques employed are similar to those known in the art for polymerizing maleimide and substituted maleimides such as N-phenyl maleimide.

Additionally, the N-propionitrile maleimides of the present invention and the N-propionitrile maleamic acid precursors may be suitable for use in the pharmaceutical and insecticidal areas owing to the presence of the nitrile group associated with the maleimide.

The compounds and methods of the present invention are illustrated by the following example.

EXAMPLE

N-(beta-propionitrile) maleamic acid was prepared as follows. Maleic anhydride (9.9 grams) was dissolved in tetrahydrofuran (20 ml) in a 100 ml round bottom flask fitted with a magnetic stirrer. Beta-aminopropionitrile (7.6 grams of 95% purity) in tetrahydrofuran (20 ml) was added dropwise to the flask which was cooled with ice. A fine suspension of crystals was formed. After warming to room temperature, the crystals were filtered, washed with tetrahydrofuran and air dried. The melting point of the crystals was 138.6 as determined by differential scanning calorimetry (DSC). The product also appeared to begin to lose the aminopropionitrile group upon melting. The infrared spectra indicated two types of carbonyl and a N-H amide bond. An 89% yield provided 15.4 grams of the maleamic acid product.

The resulting N-(beta propionitrile) maleamic acid was then used to prepare N-(beta propiontrile) maleimide. More specifically, the resulting N-(beta-propionitrile) maleamic acid was heated to 80° C. with a 3:1 ratio of acetic anhydride containing sodium acetate for a period of about 30 minutes. The resulting mass of crystals was treated with isopropanol alcohol and poured into water. After treatment with 5% sodium bicarbonate, the solution was filtered and extracted twice with chloroform. The chloroform was washed with sodium bicarbonate solution until neutral (4 washings). Upon evaporation of the chloroform, an approximately 60% yield of crude maleimide product was obtained.

The crude product was recrystallized and provided a product having a melting point of 107° C. The recrystallized product was reheated and exhibited a melting point of 103.4° C. Examination of the pan indicated sublimation of the product. The infrared spectra of the product had a single carbonyl band and no O-H bands.

The preceding example is set forth to illustrate specific embodiments of the invention and is not intended to limit the scope of the compounds, methods and compositions of the present invention. Additional embodiments and advantages within the scope of the claimed invention will be apparent to one of ordinary skill in the art.

What is claimed is:

1. A homopolymer formed from N-(beta-propionitrile) maleimide.

2. A copolymer formed from N-(beta-propionitrile) maleimide and at least one additional comonomer selected from the group consisting of styrene, substituted sytrenes, acrylonitrile, alkyl acrylates, alkyl methacrylates, maleic anhydride, maleimide and N-phenyl maleimide.

3. A copolymer formed from N-(beta-propionitrile) maleimide, and at least one additional comonomer selected from the group consisting of styrene, substituted styrene, alkyl acrylates, alkyl methacrylates, maleic anhydride and N-phenyl maleimide.

* * * * *